(12) United States Patent
Isaac et al.

(10) Patent No.: US 12,134,098 B2
(45) Date of Patent: *Nov. 5, 2024

(54) MICRODROPLET MANIPULATION METHOD

(71) Applicant: Lightcast Discovery Ltd, Cambridge (GB)

(72) Inventors: Tom Isaac, Cambridge (GB); Barnaby Balmforth, Cambridge (GB); Jasmin Conterio, Cambridge (GB); Kerr Francis Johnson, Cambridge (GB); Maciej Sosna, Cambridge (GB); Richard Ingham, Cambridge (GB); Gareth Podd, Cambridge (GB)

(73) Assignee: LIGHTCAST DISCOVERY LTD, Cambridge (GB)

( * ) Notice: Subject to any disclaimer, the term of this patent is extended or adjusted under 35 U.S.C. 154(b) by 38 days.

This patent is subject to a terminal disclaimer.

(21) Appl. No.: 17/972,825

(22) Filed: Oct. 25, 2022

(65) Prior Publication Data

US 2023/0042115 A1 Feb. 9, 2023

Related U.S. Application Data

(63) Continuation of application No. 17/429,124, filed as application No. PCT/GB2020/050280 on Feb. 7, 2020, now Pat. No. 11,504,715.

(30) Foreign Application Priority Data

Feb. 8, 2019 (EP) .................................... 19156182

(51) Int. Cl.
*B01L 3/00* (2006.01)
*C12Q 1/6869* (2018.01)

(52) U.S. Cl.
CPC ...... *B01L 3/502784* (2013.01); *C12Q 1/6869* (2013.01); *B01L 2200/0673* (2013.01); *B01L 2200/16* (2013.01); *B01L 2300/0896* (2013.01)

(58) Field of Classification Search
None
See application file for complete search history.

(56) References Cited

U.S. PATENT DOCUMENTS 11,504,715 B2 * 11/2022 Isaac ................ B01L 3/502784
2007/0241068 A1 10/2007 Pamula et al.
2012/0108721 A1 5/2012 Mazutis
2013/0210680 A1 8/2013 Derda
2015/0247192 A1 9/2015 Frayling et al.
2015/0321163 A1 11/2015 Hung
2017/0128942 A1 5/2017 Abate
2017/0175179 A1 * 6/2017 Hiddessen ........... C12Q 1/6848

FOREIGN PATENT DOCUMENTS

| EP | 3 013 987 | 11/2016 |
|---|---|---|
| EP | 3 008 207 | 8/2017 |
| WO | 2014/167323 | 10/2014 |
| WO | 2015/121675 | 8/2015 |
| WO | 2016/012789 | 1/2016 |
| WO | 2017/140839 | 8/2017 |
| WO | 2018/234446 | 12/2018 |

OTHER PUBLICATIONS

International Search Report issued Mar. 5, 2020 in International (PCT) Application No. PCT/GB2020/050280, 3 pages.
Written Opinion of the International Searching Authority issued Mar. 5, 2020 in International (PCT) Application No. PCT/GB2020/050280, 5 pages.
Extended European Search Report issued Jul. 2, 2019 in corresponding European Patent Application No. 19156182.8, 8 pages.

* cited by examiner

*Primary Examiner* — Robert T. Crow
(74) *Attorney, Agent, or Firm* — Porter Wright Morris & Arthur LLP

(57) ABSTRACT

A method of manipulating microdroplets having an average volume in the range 0.5 femtolitres to 10 nanolitres comprised of at least one biological component and a first aqueous medium having a water activity of $a_{w1}$ of less than 1 is provided. It is characterised by the step of maintaining the microdroplets in a water-immiscible carrier fluid which further includes secondary droplets having an average volume less than 25% of the average volume of the microdroplets up to and including a maximum of 4 femtolitres and wherein the volume ratio of carrier fluid to total volume of microdroplets per unit volume of the total is greater than 2:1. The method may be employed for example with microdroplets containing biological cells or with microdroplets containing single nucleoside phosphate such as are prepared in a droplet-based nucleic acid sequencer. The method is suitable for controlling for example cellular, chemical or enzymatic processes and/or microdroplet size in microdroplets or single nucleotide nucleic acid sequencing.

18 Claims, 2 Drawing Sheets

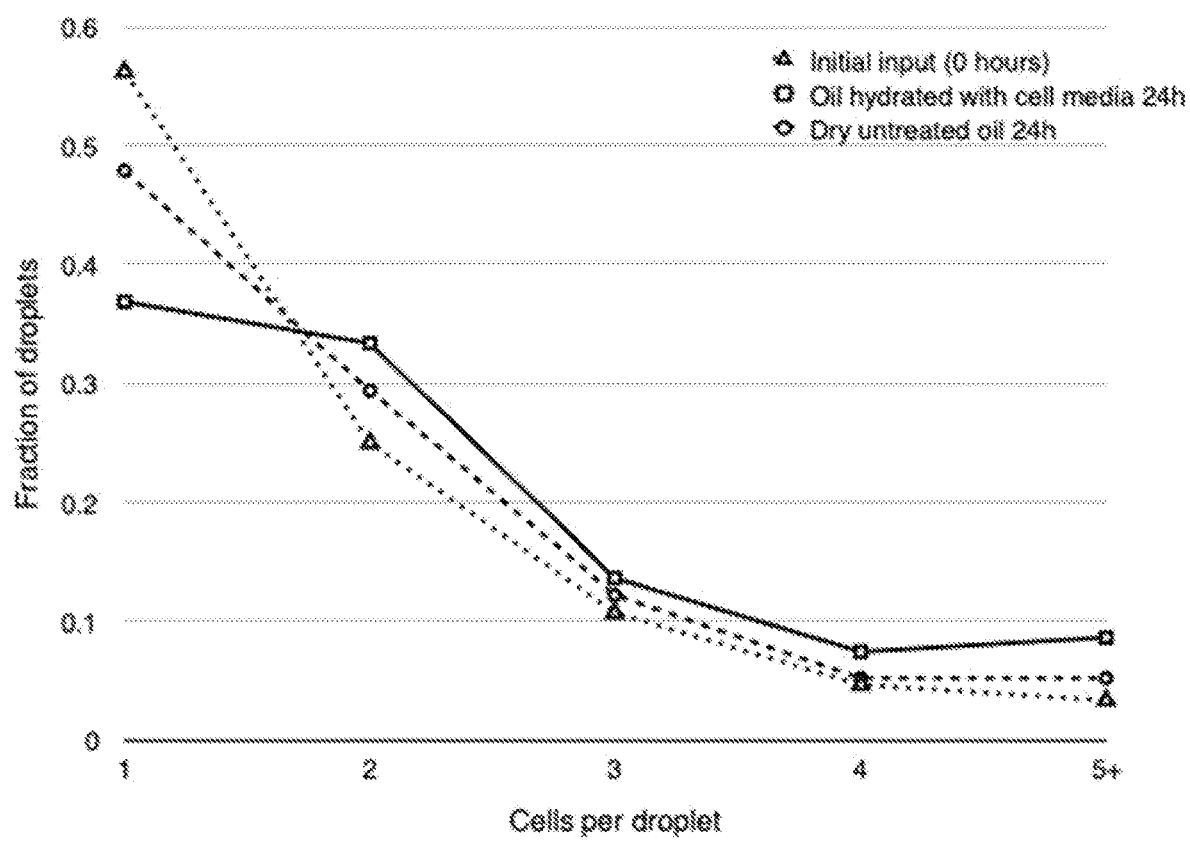

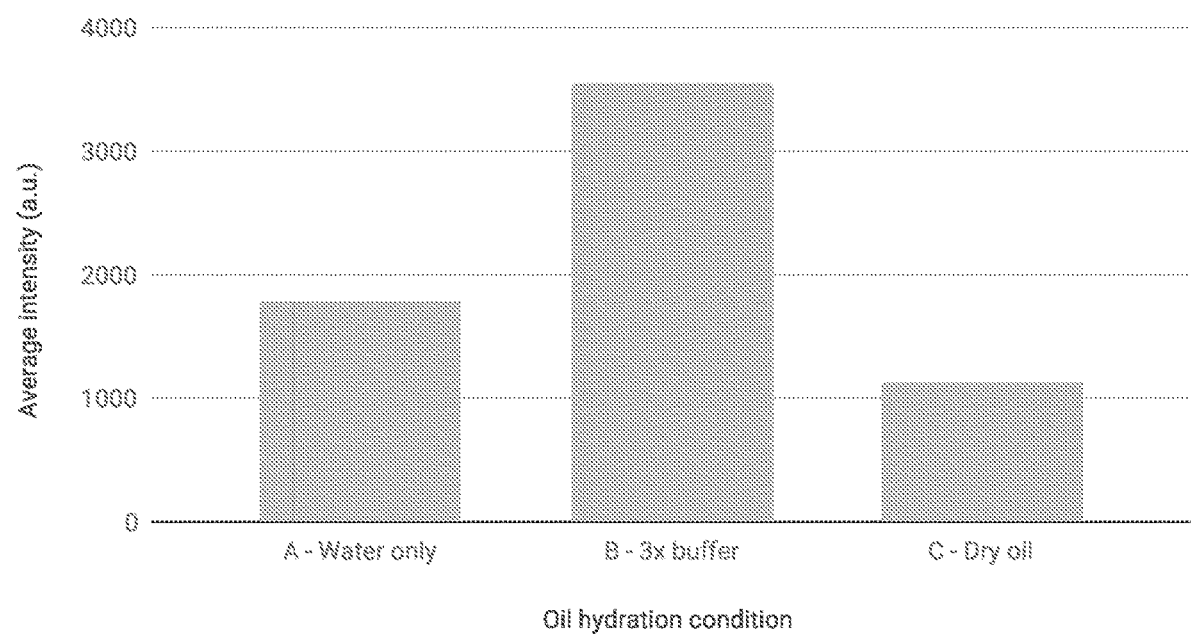

MICRODROPLET MANIPULATION METHOD

This invention relates to an improved method of manipulating aqueous microdroplets optionally containing biological cells in an immiscible carrier fluid such as an oil. It enables the size of the microdroplets to be controlled or adjusted and any enzymatic or chemical reactions occurring therein to be maintained or optimised during a given period.

In our previous patent applications, for example WO2014167323, WO2015121675, WO2016012789, WO2017140839 and PCT/EP2018066574, we have described methods in which biological components such as cells, enzymes, oligonucleotides and even single nucleotides are manipulated within microdroplets for purposes of carrying out a range of analyses including DNA and RNA sequencing and the detection and characterisation of cells and viruses. In some embodiments, these methods involve translocating microdroplets dispersed in an immiscible carrier fluid along microfluidic pathways in an analytical device using electrowetting propulsive forces or by directly printing of the microdroplets onto a substrate coated with the carrier fluid. In many instances, where the volume fraction of the microdroplets is relatively low, we have found that these microdroplets tend to undergo significant shrinkage over time which can sometimes interfere with some or all the enzymatic processes going on within. Also, in other instances it may be desirable to deliberately shrink or grow the size of the microdroplets in a part of a device as a given analysis is carried out.

We have now developed a microdroplet manipulation method which overcomes these problems. It may be used, for example, to manipulate the size and/or reactivity of the contents of microdroplets or to control chemical or enzymatic reactions occurring therein. The invention is as defined in the appended claims. According to a first aspect of the invention, there is provided a generic method of manipulating (controlling the size and/or chemical composition of the contents of) microdroplets having an average volume in the range 0.5 femtolitres to 10 nanolitres comprised of at least one biological component and a first aqueous medium having a water activity of $a_{w1}$ of less than 1 characterised by the step of maintaining the microdroplets in a water-immiscible carrier fluid which further includes secondary droplets of a second aqueous medium having an average volume less than 25% of the average volume of the microdroplets up to and including a maximum of 4 femtolitres and wherein the volume ratio of carrier fluid to total volume of microdroplets per unit volume of the total is greater than 2:1.

Without wishing to limit the scope of the invention, it is believed that the invention solves the problem by using a carrier fluid which contains very small secondary droplets which can interact with the microdroplets without adversely affecting the latter's overall characteristics or the efficacy of any detection method applied to them. When the carrier medium is an oil such a composite medium is sometimes referred to as 'hydrated oil'. An important feature in this respect is that the relative water activities of the microdroplets and the secondary droplets are controlled within certain parameters; optionally by continuous monitoring and/or a feed-back loop. Here, the water activity of an aqueous medium $(a_w)$ is defined as the ratio of the partial vapour pressure of the aqueous medium under investigation to that of pure water under STP conditions. Since water tends to diffuse along a gradient from high to low water activity, we have found that, within the constraints of our systems, when the water activity of the second aqueous medium $(a_{w2})$ is higher than that of the first aqueous medium $(a_{w1})$ the net effect is for the microdroplets to undergo expansion until the water activities of the two components equalise. Conversely, when the water activity of the second aqueous medium is higher than that of the first aqueous medium the microdroplets will tend to shrink until these water activities equalise. In one useful embodiment, the water activities of the first and second aqueous media may be the same or substantially the same so that any tendency for the microdroplets to shrink or expand is continuously counteracted. Thus, the sizes of the microdroplets may always be preserved. We have also found that, by these means, these secondary droplets can be used to assist in preserving or even enhancing any enzymatic or chemical reactions occurring in the microdroplets; for example, by using the secondary droplets to feed cell-growth components to the microdroplets at one or more points in any device employing the method. The first and second aqueous medium may have compositions which in one embodiment are identical.

Thus, in one embodiment of the invention, the water activity of the first and the second aqueous media are independently in the range from 0.9 to 1. In another embodiment, the water activity of the first aqueous medium is from 0.9 to less than 1. In yet another embodiment, the ratio of the water activities of the first and second aqueous media $(a_{w1}:a_{w2})$ is in the range 0.9:1 to 1:0.9. In certain embodiments, the secondary droplets have a water activity $a_{w2}$ which is greater than $a_{w1}$. In certain other embodiments, the secondary droplets have a water activity $a_{w2}$ which is less than $a_w1$.

One convenient way to perform the manipulation is using first and second media which are buffers; and, if required, by varying the relative compositions of the two. For example, in one application the ionic strength of the first aqueous medium is in the range from to 1 to 5 that of the second aqueous medium; preferably from 3 to 5 times. In another, the ionic strength of the second aqueous medium is in the range from to 1 to 5 times that of the first aqueous medium; preferably from 3 to 5 times. In yet another application, the ionic strengths are the same or substantially the same with the ratio of ionic strengths being in the range from 3:1 to 1:3. In one particularly useful embodiment, either or both first and second aqueous media may include glycerol as a component; for example, at differing concentrations. In another, the pHs of the first and second aqueous media are the same or similar and within the range 6.5 to 8.

As regards the secondary droplets, these have a much smaller average volume than the average value for the microdroplets and at the limit may be comprised of femto-sized droplets or micelles of the second aqueous medium emulsified within the carrier fluid and stabilised by a sheath of compatible surfactant molecules; for example, a non-ionic surfactant. In one embodiment, the size of these secondary droplets is less than 10%, preferably less than 5% of the volume of the microdroplets employed. In another, the average volume of the secondary droplets lies within the range 10 to 1% of the average volume of the microdroplets. Suitably the secondary droplets form part of a stable emulsion in the carrier fluid which in one embodiment is an immiscible oil. Suitably, the carrier fluid is selected from a mineral oil, a silicone oil or a fluorocarbon oil. The oil may also contain additional surfactants and stabilisers if required. Suitably the volume ratio of carrier fluid to total volume of the microdroplets is greater than 3:1; preferably 5:1 or greater.

The method of the invention is useful for several applications where biological cells are being analysed. One example is where a culture of immortalised mammalian cells is being caused to proliferate inside the microdroplets for the purpose of screening individual clonal copies of the cells for desirable characteristics such as protein expression or particular genetic traits. Thus in a second aspect of the invention, there is in one embodiment provided a method of causing the cellular proliferation of one or more cell types contained within a microdroplet having an average volume in the range 4 femtolitres to 10 nanolitres and comprised of an aqueous buffer comprising the steps of incubating the cell(s) inside the droplets in suitable environmental conditions and thereafter detecting the number of cells inside each droplet, characterised in that the microdroplets are suspended in an immiscible carrier fluid further comprising secondary droplets having an average volume less than 25% of the average volume of the microdroplets up to and including a maximum of 4 femtolitres and wherein the volume ratio of carrier fluid to total volume of microdroplets per unit volume of the total is greater than 2:1.

In another embodiment, there is also provided a method of detecting one or more phenotypic traits, genetic traits or protein expression profiles of a cell under consideration, that cell being contained within a microdroplet having an average volume in the range 4 femtolitres to 10 nanolitres and comprised of an aqueous growth media comprising the steps of labelling a target derived from the cell(s) with a fluorescent probe and thereafter detecting an output from the probe characterised in that the cell-containing microdroplets are suspended in an immiscible carrier fluid further comprising secondary droplets having an average volume less than 25% of the average volume of the microdroplets up to and including a maximum of 4 femtolitres and wherein the volume ratio of carrier fluid to total volume of microdroplets per unit volume of the total is greater than 2:1. Fluorescent probe molecules suitable for this purpose are well known and include fluorescently labelled antibodies, FRET reporter probes and enzyme-labelled antigens which are degraded in the presence of a target protein.

In another embodiment, there is provided a method of analysing an oligonucleotide derived from a biological cell contained within a microdroplet having an average volume in the range 4 femtolitres to 10 nanolitres and further comprised of an aqueous buffer comprising the steps of labelling the oligonucleotide with a fluorescent hybridisation probe and thereafter detecting the corresponding fluorescence characterised in that the microdroplets are suspended in an immiscible carrier fluid further comprising secondary droplets having an average volume less than 25% of the average volume of the microdroplets up to and including a maximum of 4 femtolitres and wherein the volume ratio of carrier fluid to total volume of microdroplets per unit volume of the total is greater than 2:1. In certain embodiments, the oligonucleotide can be derived from the DNA or RNA of a cell.

Fluorescent hybridisation probes which can be used for this purpose are well-known in the art and include molecular beacons, TaqMan® probes, Scorpion® probes and LNA® probes. Methods for detecting the fluorescence arising in all these embodiments are well-known to one of ordinary skill in the art; for example, those methods employing a source of incident electromagnetic radiation (laser, LED and the like) and a corresponding photodetector for detecting fluorescence photons and outputting a data-stream which can be analysed using microprocessor algorithms.

Thus, the target in these methods may be the cell(s) themselves, one or more oligonucleotides derived therefrom or a product such a protein which is expressed by the cell(s) when cultured within the microdroplet itself. Such oligonucleotides may be generated from the cell(s) by lysis.

The method of the invention may also be suitably employed in connection with biological components which are non-cellular or cell-free although in one embodiment it may be used to manipulate nucleic acids or components thereof which have been previously derived from biological cells. Thus in a third aspect of the invention there is provided there is provided a method of manipulating the size and/or reactivity of the contents of microdroplets having an average volume in the range 0.5 femtolitres to 10 nanolitres; the microdroplets being comprised of at least one biological component and a first aqueous medium free of biological cells having a water activity of $a_{w1}$ of less than 1 characterised by the step of maintaining the microdroplets in a water-immiscible carrier fluid which further includes secondary droplets comprised of a second aqueous and having an average volume less than 25% of the average volume of the microdroplets up to and including a maximum of 0.5 femtolitres and wherein the volume ratio of carrier fluid to total volume of microdroplets per unit volume of the total is greater than 2:1.

The method of the third aspect of the invention is useful for a number of applications where the biological component is a single nucleotide; for example, a single nucleoside triphosphate or single nucleoside monophosphate derived from a target nucleic acid. For example, the method may be advantageously used with one of the sequencing methods we have previously described including but not limited to those described EP3013987 or in the other above-mentioned patent applications to which the reader is directed. Thus, in a third aspect, there is provided a method of sequencing comprising the steps of progressively digesting by pyrophosphorolysis a nucleic acid analyte into an ordered stream of nucleoside triphosphate molecules and generating therefrom a corresponding ordered stream of microdroplets having an average volume in the range 0.5 femtolitres to 10 nanolitres and each comprised of one of the nucleoside triphosphate molecules and aqueous buffer; reacting each nucleoside triphosphate molecule within each microdroplet with a nucleobase-specific fluorescent probe and thereafter detecting the corresponding fluorescence associated with each microdroplet thereby identifying the nucleobase characterised in that the microdroplets are suspended in an immiscible carrier fluid further comprising secondary droplets having an average volume less than 25% of the average volume of the microdroplets up to and including a maximum of 0.5 femtolitres and wherein the volume ratio of carrier fluid to total volume of microdroplets per unit volume of the total is greater than 2:1.

Fluorescent probes suitable for use in this application have been describe by us in our previous patent applications; for example, WO2016012789 and subsequently published applications to which the reader is directed. These probes are characterised by (a) being non-fluorescing in their unused state and (b) being capable of undergoing exonucleolysis once used to produced fluorophores in a detectable state attached to single nucleoside monophosphates. The fluorescence arising may be detected and analysed as described above.

In all these additional aspects of the invention it is preferred that the ratio of the water activities of the first and second aqueous media associated with respectively the microdroplets and the secondary droplets is in the range 0.9:1 to 1:0.9; preferably 0.95:1 to 1:0.95 and for example 1:1.

The advantageous effect of hydrating the carrier phase as described above is now illustrated by the following Examples.

Example 1 (Cell Growth)

Continuous oil phase material is prepared by mixing 99 parts of a Hydrofluoroether continuous phase with 1 part of a fluorinated surfactant. A growth-media-treated carrier phase is prepared by mixing an aliquot of RPMI 1640 media (Thermo Fisher Scientific, UK) with an equal volume of the oil/surfactant mixture and agitating the mixture for 24 hours at 37° C. to form a polydisperse emulsion. This emulsion is then left to stand until it spontaneously fractionates to form an upper phase comprising large droplets and undispersed plugs of aqueous growth media, and a lower phase containing only the smallest vesicles of growth media suspended in the oil phase which is additionally now saturated with dissolved aqueous media. This lower phase is removed from the vessel using a pipette and retained for later use.

Jurkat E6-1 T-cell lymphoma cells (ATCC, Virginia, USA) are suspended in RPMI media at a concentration of 8E6 cells/ml. This media and cells are then flowed through an emulsifying apparatus to form droplets of 50 um diameter, with cells dispersed throughout the droplets. The outer carrier phase for the emulsion is a hydrofluoroether oil mixed with 1% of a suitable surfactant to stabilise the droplets in solution. The emulsion thus formed spontaneously fractionates to form a layer of densely packed monodisperse aqueous droplets floating at the top of a column of continuous oil/surfactant mixture. This emulsion is then evenly dispersed by gentle mixing and divided in to three aliquots containing droplets and the carrier phase.

One aliquot (the initial reference) is immediately transferred in to a haemocytometer flow cell and the droplets therein are inspected using a 20× magnification optical microscope. The cell occupancy of each droplet is recorded by counting the number of distinct cells in each droplet. Empty droplets are disregarded.

The second aliquot is allowed to fractionate once more, and the lower carrier phase removed using a pipette. An equivalent volume of the earlier treated carrier phase is introduced to the sample to replace the removed untreated carrier phase. The third aliquot is left unaltered. Both the second and third aliquots are then transferred in to partially sealed vessels which permit gas permeation between the vessel and its surroundings. Both vessels are placed in to an environment-controlled CO2 incubator set to contain 5% CO2/air mixture, 95% humidity and 37° C. set temperature. The aliquots are incubated for 24 hours These aliquots are then removed from the incubator and introduced to a haemocytometer for inspection and analysis in the same way as the reference aliquot. The change in the cell population-distribution after the incubation (characteristic of cell proliferation) can then be compared between the different oil treatments.

FIG. 1 compares the results obtained after 24 hours culture relative to baseline measurement at zero and 24 hours with no hydration of the oil. Cell growth is expressed here as a fraction of the droplets containing more than one cell. It will be seen that, relative to the baseline cell growth, an improvement occurs when the oil is hydrated with the cell culture medium.

Example 2 (Reactivity)

A continuous hydrated oil phase is prepared by mixing 99 parts of a light mineral oil with 1 part of a pegylated surfactant by weight. The oil is placed on rotator overnight to fully mix oil and surfactant. Hydrated oil is prepared by mixing 5 parts of the oil with 3 parts of the aqueous hydrating phase, consisting of either the same saline buffer used in the disperse emulsion phase or just water. The mixture is rotated overnight at 50C and then for 60 min at 70C. The emulsion is left to stand for 15 min. The upper portion of the emulsion is aliquoted, and the aliquots are then centrifugated to adjust the hydration level of the oil, with longer centrifugation times leading to lower hydration levels. The hydration level is measured using a Karl Fisher titrator. Once the correct hydration level is achieved, usually 500-1000 ppm, the supernatant of the aliquots is pipetted into new tubes which are frozen until used.

A polydisperse emulsion of droplets is produced by mixing 8 parts of the oil (either hydrated or not hydrated) with 1 part of the disperse aqueous phase by volume followed by mixing on a vortex mixer for 5 min and centrifugation for 1 min at 400 RPM. The upper half of the mixture is pipetted into a new tube which is centrifuged for 5s. The emulsion is pipetted from the bottom of the tube for further use.

For measurements of the enzymatic activity, the disperse aqueous phase described above consists of the single nucleotide detection chemistry as previously described and exemplified in EP3013987.

For measurement of the fluorescent intensity the emulsion is sandwiched between two transparent substrates separated by spacers corresponding to the average emulsion droplet size. The fluorescent signal emitted from each emulsion droplet, upon excitation with light of an appropriate wavelength range, is measured together with the diameter of droplet which is collected from a brightfield image of the emulsion.

The data presented as a histogram in FIG. 2 shows the average fluorescent intensity of 6 um droplets, which have been incubated in oil with no hydration ('Dry oil'), in oil hydrated with water ('Water only') or oil hydrated with three times the buffer concentration of the droplets ('3× buffer'). Droplets incubated in oil with no hydration show very low intensity above the background which for these samples is approximately 1000 counts. Those incubated in oil hydrated with water show an increased intensity compared to droplets incubated in oil with no hydration. Incubation of droplets in oil hydrated with three times the buffer concentration shows a further increase in average intensity. This demonstrates that both oil hydration can be used to maintain enzymatic reactivity in these droplets.

Example 3 (Droplet Size Effect)

Microdroplets are deposited on a substrate immersed in a continuous oil phase as for example previously described in EP3008207 to which the reader is directed.

The continuous hydrated oil phase is prepared by mixing 99 parts of paraffin oil with 1 part of a pegylated surfactant by weight. The oil is placed on rotator overnight to fully mix oil and surfactant. Hydrated oil is prepared by mixing 5 parts of the oil with 3 parts of the aqueous hydrating phase, consisting of water with or without 4% glycerol. The mixture is rotated overnight at 50C and then for 60 min at 70C. The emulsion is left to stand for 15 min. The upper portion of the emulsion is aliquoted, and the aliquots are then centrifugated to adjust the hydration level of the oil, with longer centrifugation times leading to lower hydration levels. The hydration level is measured using a Karl Fisher titrator. Once the correct hydration level is achieved, usually 500-1000 ppm, the supernatant of the aliquots is pipetted into new tubes which are frozen until used.

The disperse aqueous phase consists of water with or without 4% glycerol. The deposited droplets are subjected to an incubation cycle at 70C for 115 min. The emulsion droplet diameters are then measured from a brightfield microscope image and compared to measured diameters prior to the incubation cycle to infer droplet shrinkage or growth.

The data presented below shows the average volume change of droplets upon a high temperature incubation step as a function of percentage of glycerol in the oil hydration and droplets respectively. In the reference sample, if glycerol is not present in either the oil hydration nor in the droplets, the droplets shrink on average. If the droplets contain glycerol whereas the oil hydration does not, the droplets grow relative to the reference because the addition of glycerol to the droplets causes the water activity in the oil to be higher than the water activity in the droplets. The reverse happens when glycerol is added to the oil hydration but not the droplets. Droplets shrink relative to the reference due to a higher water activity in the droplets compared to the oil. This shows that the specific content of the droplets and the oil hydration can be used to control droplet shrinkage and growth.

| % glycerol in oil hydration | % glycerol in droplets | Droplet volume change |
|---|---|---|
| 0 | 0 | −30% (shrink) |
| 0 | 4 | +44% (grow) |
| 4 | 0 | −51% (shrink) |

The invention claimed is:

1. A method of manipulating microdroplets having an average volume in the range from 0.5 femtolitres to 10 nanolitres comprised of at least one of an oligonucleotide or a product and a first aqueous medium having a water activity of $a_{w1}$ of less than 1 comprising a step of maintaining the microdroplets in a water-immiscible carrier fluid which further includes secondary droplets comprised of a second aqueous medium having an average volume less than 25% of the average volume of the microdroplets up to and including a maximum of 4 femtolitres and wherein the volume ratio of carrier fluid to total volume of microdroplets per unit volume of the total is greater than 2:1.

2. The method according to claim 1, wherein the water-immiscible carrier fluid is a hydrated oil, a mineral oil, a silicone oil or a fluorocarbon oil.

3. The method according to claim 1, wherein the secondary droplets have a water activity $a_{w2}$ which is greater than $a_{w1}$.

4. The method according to claim 3, wherein the ionic strength of the second aqueous medium is in the range from 1 to 5 times that of the first aqueous medium.

5. The method according to claim 1, wherein the secondary droplets have a water activity $a_{w2}$ which is less than $a_{w1}$.

6. The method according to claim 5, wherein the ionic strength of the first medium is in the range from 1 to 5 times that of the second aqueous medium.

7. The method according to claim 1, wherein water activities $a_{w1}$ and $a_{w2}$ are the same.

8. The method according to claim 1, wherein $a_{w1}$ and $a_{w2}$ are independently in the range 0.9 to 1.

9. The method according to claim 1, wherein the average volume of the secondary droplets is less than 10% of the average volume of the microdroplets.

10. The method according to claim 1, wherein at least one of the first and second aqueous media further comprises glycerol.

11. The method according to claim 1, wherein the biological component is selected from the group consisting of a single nucleoside triphosphate derived from a target nucleic acid, an oligonucleotide derived from the DNA or RNA of a cell, an enzyme, and a cell.

12. The method as claimed in claim 11, wherein first and/or second aqueous media are buffers.

13. The method according to claim 1, wherein the carrier fluid is a composite medium comprising a hydrated fluorocarbon oil.

14. A method of manipulating microdroplets having an average volume in the range from 0.5 femtolitres to 10 nanolitres comprised of at least one biological component and a first aqueous medium having a water activity of $a_{w1}$ of less than 1 comprising a step of maintaining the microdroplets in a water-immiscible carrier fluid which further includes secondary droplets comprised of a second aqueous medium emulsified within the carrier fluid and stabilized by a sheath of compatible surfactant molecules; the secondary droplets having an average volume less than 25% of the average volume of the microdroplets up to and including a maximum of 4 femtolitres and wherein the volume ratio of carrier fluid to total volume of microdroplets per unit volume of the total is greater than 2:1.

15. The method according to claim 14, wherein the surfactant is a molecules are non-ionic.

16. The method according to claim 14, wherein the surfactant is a molecules are fluorinated.

17. The method according to claim 14, wherein the surfactant is a fluorinated surfactant and the carrier fluid is a composite medium comprising a hydrated fluorocarbon oil.

18. A method of manipulating microdroplets for carrying out analysis including DNA sequencing having an average volume in the range from 0.5 femtolitres to 10 nanolitres comprised of components including a DNA strand and an enzyme and a first aqueous medium having a water activity of $a_{w1}$ of less than 1 comprising a step of maintaining the microdroplets in a water-immiscible carrier fluid which further includes secondary droplets comprised of a second aqueous medium having an average volume less than 25% of the average volume of the microdroplets up to and including a maximum of 4 femtolitres and wherein the volume ratio of carrier fluid to total volume of microdroplets per unit volume of the total is greater than 2:1.

* * * * *